United States Patent
Geissler et al.

(10) Patent No.: US 11,786,145 B2
(45) Date of Patent: Oct. 17, 2023

(54) SYSTEM AND METHOD FOR DETERMINING ANIMAL BODY SURFACE AREA AND SUBSEQUENTLY DETERMINING ANIMAL HEALTH STATUS

(71) Applicant: Geissler Companies, LLC, Minneapolis, MN (US)

(72) Inventors: Randolph Keith Geissler, Hudson, WI (US); Steven Arthur Lewis, Bloomington, MN (US)

(73) Assignee: Geissler Companies, LLC, Minneapolis, MN (US)

( * ) Notice: Subject to any disclaimer, the term of this patent is extended or adjusted under 35 U.S.C. 154(b) by 557 days.

(21) Appl. No.: 16/401,978

(22) Filed: May 2, 2019

(65) Prior Publication Data

US 2019/0336041 A1  Nov. 7, 2019

Related U.S. Application Data

(60) Provisional application No. 62/665,820, filed on May 2, 2018.

(51) Int. Cl.
*A61B 5/107* (2006.01)
*A61B 5/00* (2006.01)
(Continued)

(52) U.S. Cl.
CPC .......... *A61B 5/1072* (2013.01); *A61B 5/0022* (2013.01); *A61B 5/0064* (2013.01);
(Continued)

(58) Field of Classification Search
CPC ... A61B 5/0064; A61B 5/1072; A61B 5/0507; A61B 5/1079; A61B 5/1077;
(Continued)

(56) References Cited

U.S. PATENT DOCUMENTS 5,412,420 A   5/1995  Ellis
5,483,441 A   1/1996  Scofield
(Continued)

OTHER PUBLICATIONS

Buranakarl, Chollada, et al. "Estimation of body weight and body surface area in swamp buffaloes using visual image analysis." Journal of Buffalo Science 1.1 (2012): 13-20. (Year: 2012).*
(Continued)

*Primary Examiner* — Devin B Henson
(74) *Attorney, Agent, or Firm* — Berg Hill Greenleaf Ruscitti LLP (57) ABSTRACT

The invention includes a system to determine body surface area (BSA) or volume of an animal that can be used to determine a health status of the animal. The system has a plurality of integrated measuring devices such as radar or infrared sensors. The measuring devices are mounted within a confined space. A plurality of measurements is taken along vertically oriented sections or slices of the animal as the animal passes by the confined space. The measurements are combined and numerically converted to BSA or volume estimations. The health status can be derived as a direct relation to BSA or volume, or changes in BSA or volume over a selected time period.

21 Claims, 2 Drawing Sheets

(51) Int. Cl.
  *A61B 5/0507* (2021.01)
  *A61B 5/0205* (2006.01)
(52) U.S. Cl.
  CPC ........ *A61B 5/02055* (2013.01); *A61B 5/0507* (2013.01); *A61B 2503/40* (2013.01)
(58) Field of Classification Search
  CPC ...... A61B 2503/40; A01K 29/00; G06T 7/62; A22B 5/007
  See application file for complete search history.

(56) References Cited

U.S. PATENT DOCUMENTS

| | | | |
|---|---|---|---|
| 5,673,647 | A | 10/1997 | Pratt |
| 6,625,302 | B2 | 9/2003 | Kalscheur et al. |
| 6,974,373 | B2 | 12/2005 | Kriesel |
| 7,128,024 | B2 | 10/2006 | Doyle, II |
| 7,214,128 | B2 | 5/2007 | Kriesel |
| 7,399,220 | B2 | 7/2008 | Kriesel et al. |
| 7,711,151 | B2 | 5/2010 | Jurk |
| 7,853,046 | B2 | 12/2010 | Sharony |
| 8,036,429 | B2 | 10/2011 | Doyle, II |
| 8,351,656 | B2 | 1/2013 | Spicola et al. |
| 8,425,434 | B2 | 4/2013 | Mulder |
| 8,588,476 | B1 | 11/2013 | Spicola, Jr. |
| 8,659,764 | B2 | 2/2014 | Hatzilias et al. |
| 8,755,570 | B2 | 6/2014 | Gomas et al. |
| 8,787,621 | B2 | 7/2014 | Spicola, Sr. et al. |
| 8,885,891 | B2 | 11/2014 | Tofman et al. |
| 9,084,411 | B1 | 7/2015 | McGlone et al. |
| 9,104,906 | B2 | 8/2015 | McVey |
| 9,142,028 | B2 | 9/2015 | Banhazi et al. |
| 9,167,800 | B2 | 10/2015 | Spicola, Jr. |
| 9,311,556 | B2 | 4/2016 | Banhazi et al. |
| 9,341,464 | B2 | 5/2016 | Kimmel |
| 9,521,829 | B2 | 12/2016 | McGlone et al. |
| 9,737,239 | B2 | 8/2017 | Kimmel |
| 9,936,670 | B2 | 4/2018 | Foresman et al. |
| 10,045,511 | B1 | 8/2018 | Yarden et al. |
| 10,098,327 | B2 | 10/2018 | Laurence et al. |
| 10,149,617 | B2 | 12/2018 | Couse |
| 10,154,654 | B2 | 12/2018 | Van Der Kamp et al. |
| 10,412,935 | B2 * | 9/2019 | O'Connell .......... A01K 29/005 |
| 2003/0226522 | A1 | 12/2003 | Thibault |
| 2004/0023612 | A1 | 2/2004 | Kriesel |
| 2006/0048720 | A1 | 3/2006 | Kajihara et al. |
| 2007/0288249 | A1 | 12/2007 | Rowe et al. |
| 2010/0277571 | A1 | 11/2010 | Xu et al. |
| 2014/0286540 | A1 | 9/2014 | Hatzilias et al. |
| 2016/0295838 | A1 | 10/2016 | Van Der Kamp et al. |
| 2017/0196203 | A1 | 7/2017 | Huisma et al. |
| 2018/0160649 | A1 | 6/2018 | Hicks et al. |
| 2018/0206448 | A1 | 7/2018 | Madhusudan et al. |
| 2018/0220984 | A1 | 8/2018 | Brauner et al. |
| 2018/0242558 | A1 | 8/2018 | O'Connell |

OTHER PUBLICATIONS

International Search Report and Written Opinion dated Jun. 20, 2019 in International Application No. PCT/US19/30451, filed on May 2, 2019, 7 pages.

Theurer, M. E., et al.; "Effect of Mannheimia haemolytica pneumonia on behavior and physiologic responses of calves during high ambient environmental temperatures"; Journal of Animal Science; May 8, 2013; 15 pages.

Theurer, Miles E., et al.; "Effect of transportation during periods of high ambient temperature on physiologic and behavioral indices of beef heifers"; Mar. 3, 2013; 10 pages.

Theurer, Miles E., et al.; Relationship between rectal temperature at first treatment for bovine respiratory disease complex in feedlot calves and the probability of not finishing the production cycle; Dec. 1, 2014; 7 pages.

Theurer, BS, et al.; "Effects of weather variables on thermoregulation of calves during periods of extreme heat"; Mar. 2014; 5 pages.

Office Action in the counterpart Canadian patent application 3,098,539 dated Nov. 23, 2021, 2 pages.

Office Action in the counterpart Canadian patent application 3,098,539 dated Jan. 20, 2023, 5 pages.

* cited by examiner

SYSTEM AND METHOD FOR DETERMINING ANIMAL BODY SURFACE AREA AND SUBSEQUENTLY DETERMINING ANIMAL HEALTH STATUS

CROSS-REFERENCE TO RELATED APPLICATION

This application claims the benefit of U.S. Provisional Application No. 62/665,820, filed May 2, 2018, which is incorporated herein in its entirety by reference.

FIELD OF THE INVENTION

The invention relates to determining measured parameters for animals such as livestock and more particularly, to a system and method that reliably measures body surface area or volume in which the body surface area or volume measured is used to directly determine a health status of the animal.

BACKGROUND OF THE INVENTION

It is known to take measurements of cattle and other livestock to determine when a particular animal is ready for harvesting. Along with weight, some prior art references disclose methods of taking measurements of cattle to determine optimal characteristics of the animal prior to harvesting.

One reference that discloses a system and method for cattle measurement is the U.S. Pat. No. 6,625,302. The reference specifically addresses a system for calculating one or more dimensions of an animal. The system comprises at least three fiducial reference points, each having different X, Y, and Z coordinates in a 3-dimensional space. At least two sensors are used for obtaining dimensional measurements of the fiducial reference points and the animal from at least two different fields of view. In one embodiment, the at least two different fields of view are at least a side view and a top view. The system also comprises a processing system configured to receive the dimensional measurements from the at least two sensors and calculate one or more dimensions of the animal by relating positions of animal features to known locations of the fiducial reference points. The system also may create and measure a 3-dimensional image of the animal.

Another reference disclosing a method of measuring an animal is the U.S. Pat. No. 5,673,647. The reference teaches an automated method and system for providing individual animal electronic identification, measurement and value based management of cattle in a large cattle feedlot. A computer system is integrated with automatic individual animal identification, multiple measurement and re-measurement systems with automatic data input, and a cattle handling and sorting system. Animals are individually identified and measured by weight and external dimensions. Characteristics of internal body tissue are also analyzed. The weight, dimensions, and body tissue information is used with other animal physiological characteristics and historical data to calculate various parameters including an optimum slaughter weight, an economic end point, and a marketing date for shipment to a packing plant. After measurement, individual animals are sorted by direction of the computer in response to calculations from the measurements. The computer system also calculates from individual animal data and other data each animal's pro rata share of total feed intake for the animal's feed group fed. The computer system stores individual animal measurement, performance and location data, which is used by management to select animals for shipment from the feedlot for slaughter at the optimum time. Following an animal's shipment to a slaughter facility, its identification in the computer system is used to correlate the live animal physical characteristics and performance data to the measured and evaluated carcass characteristics data obtained during the slaughter process. A database may be built to more accurately identify and measure value-based characteristics in subsequent animals produced and fed for more effective value-based selection and management of the animals.

U.S. Pat. Nos. 7,214,128 and 7,399,220 disclose methods for measuring the physical characteristics of livestock animals such as cattle and hogs. The apparatus of the invention includes a plurality of strategically positioned cameras that are used to obtain data concerning volumetric, curvilinear (surface) and linear measurements of livestock animals such as cattle and hogs and the full carcasses thereof. In accordance with the method of the invention, the data is analyzed to provide information that substantially assists the commercial producer of livestock animals in producing a high-quality end product for the consumer while adding profitability to the enterprise.

U.S. Pat. No. 5,483,441 discloses a method to evaluate an animal to determine characteristics or traits, specifically, an image recording system used to obtain physical measurements of an animal. An animal is evaluated as it moves through first and second scenes that correspond to different first and second fields of view. Images are acquired of the first scene evaluation at a selected time and a second scene evaluation image representation of an image of the second scene at substantially the same selected time. Each scene evaluation image representation includes portions that correspond to an animal image portion and a remainder image portion which is defined by excluding the respective animal image portion. After acquiring the first and second scene evaluation image representations, the invention constructs corresponding first and second evaluation image segregation representations. The first and second evaluation image segregation representations segregate portions that correspond to at least a part of the first and second scene image animal image portions from portions that correspond to the first and second scene image remainder image portions. With the first and second image segregation representations defined, a plurality of selected parameters is ascertained. The plurality of selected parameters form selected animal indicia that are used to evaluate the animal.

Despite the number of references that disclose taking measurements of cattle to determine when an animal may reach an optimal size and weight for harvesting, none of the prior art directly relates the body surface area (BSA) or volume of an animal with a health status of the animal.

Considering the importance of determining the health of an animal during its growth cycle prior to harvesting, it is an improvement over existing technologies to be able to accurately measure the BSA or volume of an animal and then to determine if there are health risks associate with abnormal or out of range BSA or volume measurements. It is also an improvement over the prior art to be able to determine animal health under a BSA or volume analysis and not having to rely on existing standard measurements such as weight or body temperature. These standard measured parameters such as temperate and weight may not be the best indicator of health in some circumstances. As set forth below, the invention provides both of these improvements

SUMMARY OF THE INVENTION

The invention in a first embodiment relates to determining the BSA or volume of an animal, and more particularly, to a system and method that reliably measures body surface area or volume for ultimately determining the health status of an animal. Hereinafter, the term "BSA" shall also be interpreted to include volume since volume can be directly determined from a BSA calculation.

Determining a health status according to other embodiments of the invention may include a BSA measurement coupled with a weight measurement. According to one aspect of determining the health status, this may be achieved by determining a BSA to weight ratio in which ratio values correspond directly to descriptive health status indicators.

The system of the invention includes a plurality of electronic measuring devices or measuring sensors that are capable of precisely measuring short distances between parts of an animal being measured and reference points where measurements are made. According to one preferred embodiment of the invention, the measuring devices may include pulse coherent radar (PCR) sensor devices. PCR sensor devices can be manufactured as fully integrated with both transmitter and receiver antennae. A PCR sensor device emits a pulsed radar wave or beam and then measures the time of flight and magnitude of reflections from the object that distance is being measured. One example of a PCR sensor device that may be used in the present invention is a radio frequency (RF) integrated circuit (IC) sensor radar 60 GHz, 50-FCCSP (5.5×5.2), part number A111, manufactured by Acconeer AB of Lund, Sweden. There are many advantages of using PCR sensor devices in the present invention. PCR sensor devices are capable of distance measurement accuracy in millimeters, and can provide nearly continuous measurements, thus decreasing sample times between measurements. Radio waves are not affected by ambient lighting conditions or noise. A PCR radar device can be fully encapsulated within an opaque housing whereas other sensor devices may require windows for passage of emitted and reflected measurement beams.

Another type of measuring system that could be used in the present invention includes integrated infrared (IR) laser and detector measuring devices each having sensor circuitry such as a VL53L0X sensor made by ST Microsystems. The sensor circuitry within the IR measuring devices includes an IR laser emission source, an IR sensor or detector element, a microcontroller, and an optional radio. The microcontroller controls operation of the sensor/measuring device and communicates with a main controller of the system which receives and processes data signals for each of the measuring devices.

A radio communication protocol may be used between measuring devices if a sensor element of a particular measuring device is not located near a corresponding microcontroller or near other sensors. A normal configuration would therefore be to adopt wired connections between the measuring devices and between the sensor circuitry and emitters for each measuring device.

According to one particular configuration of IR measuring in which an IR measuring sensor is used a measurement "cone" of an emitted IR laser may be approximately 15° with a range of between about 0 to 2 meters. This range is adequate for taking measurements circumferentially around an animal as it passes through a typical chute width.

It shall be understood that the terms "sensors", "measuring sensors", or "measuring devices" used hereinafter, mean any type of electronic measuring device that functions to measure and record distances. The two examples referred to above, namely PCR radar sensors and IR sensors, are but two types of electronic measuring sensors that can be used with the present invention. Therefore, unless defined otherwise, these terms shall be broadly construed to include all types of electronic measuring devices.

The measuring devices are mounted within a confined area such as a cattle chute to accurately measure the circumference or periphery of an animal at numerous times as the animal passes through the chute. The measuring devices are preferably mounted within a protective measurement frame that is attached to or is part of the chute structure. The frame may include a pair of spaced vertical posts in which the spacing between the posts defines the chute through which an animal passes for measurement. However, this is but one example configuration for mounting of the measuring devices and the measurement frame can be arranged in any desired orientation that allows the measuring devices to conduct measurements around selected circumferential portions of an animal.

Measurements are preferably taken along a vertical plane or "slice" of the animal which yields an accurate and repeatable circumferential measurement. A plurality of vertical plane measurements are taken with known or approximated distances that the animal has travelled through the chute over a known period of time. The vertical plane measurements taken are then used within geometrical calculations to determine a body surface area of the animal or volume of the animal. Front and rear endpoints of the animal may optionally be measured to accurately determine the length of the animal, as well as upper height and lower belly measurements to accurately determine upper and lower bounds within the circumferential data point measurements.

Each sensor is spaced along a vertical height adjacent to a path along which the animals pass. For example, if the cattle chute has the spaced vertical posts, the posts serve to direct or channel the animals through a confined space that has the sensors mounted close by. Preferably, the sensors operate in opposing geometric pairs to account for differential sideways or transverse movement of the animal as it passes through the chute. The sensor pairs are controlled so that each sensor pair is read at the same time that enables a differential distance to be determined at any point in time between the sensor pairs. Similarly, sensors may be positioned in the opposing geometric pairs for vertical measurements so that an accurate height and lower belly measurement can be taken. The number of sensor pairs used will determine the number of measurement points taken. The greater number of measurement points taken, the more accurate the interpolation becomes of the BSA calculations for the animal measured. According to this arrangement of the measuring sensors, the distances measured are therefore substantially perpendicular to the direction of travel of the animal as it passes the measuring sensors. This perpendicular arrangement allows a number of vertical measurement "slices" to be taken along the entire length of the animal.

Other sensors however may be used in the chute area, for example, to detect when the animal arrives and when the hindquarters of the animal pass. An arrival sensor can be programmed to turn on the other sensors for purposes of initiating the plurality of vertical plane measurements to be taken as the animal moves through the chute.

The sensors of the system can be controlled independently of one another, but preferably are controlled by a single master controller that controls when each of the sensors are activated to take a reading. The master controller combines data from all of the sensor measurements and stores the data for later use in determining the BSA, volume, and other measurements. The master controller is capable of communicating with other elements within a communication system. Therefore, the master controller may utilize various radio protocols including Bluetooth, LoRa, and short range radio protocols. The master controller may also communicate with other independent diagnostic or identifying devices for determining animal health status and the identity of a particular animal. These other devices may include, for example, digital stethoscopes and RFID readers that may be employed in an environment such as a feed yard.

The master controller can be a dedicated computing device, or master controller functions can be handled by one or more computing devices used at the location where the sensor are installed, such as a feedlot. In the environment of a feedlot, the master controller functions can be handled by, for example, by a chute-side computer that monitors and records the intake of animals arriving at a feedlot location, or a main computer within the feedlot that handles other feed lot operations.

According to a method of the invention, an animal enters a chute or other type of confined area in which a plurality of measuring sensors are located. The measuring sensors are spaced from one another in a vertical orientation. The sensors each emits a wave/beam that is oriented substantially perpendicular to the path of travel of an animal entering the chute. If PCR sensor devices are used, each emits an RF wave/beam whereas if IR sensors are used, each emits a burst of IR light. As the animal passes through the chute, a plurality of measurements is therefore taken along the vertical planes or "slices". The measurements are mathematically manipulated to determine a BSA of the animal. Each portion of the animal can be measured to include the head, torso, and rear of the animal which differs from many prior art systems in which much fewer measurements are taken and therefore, greater numerical assumptions have to be made to estimate a BSA or volume.

In order to track the historical weight gain or loss of an animal and other indicators of animal health, the measuring sensors can be located where the animal eats or drinks on a daily basis. For example, a measurement frame having two posts with opposing pairs of measuring sensors mounted therein can be located at any desired location where the animal is found, such as near a feed trough or water trough. In addition to measuring sensors, an RFID reader can be mounted to the measurement frame so that as an animal passes, the RFID tag of the animal is read and the measurement data recorded by the sensors is then directly associated with the animal. The measurement frame can be supplemented with fencing or other barriers to channel or direct the animal through the measurement frame in order for the animal to access the water or feed trough. A historical portfolio for each animal can be created in which incremental BSA and weight can be tracked. Differences in these measured parameters can provide an early indication of deteriorating health, health recovery, and other health statuses. Particularly in a feedlot setting, it is advantageous to obtain early detection of a sick animal.

According to another preferred embodiment of the invention, it includes a system for determining a health status of an animal by measuring the BSA of the animal and then making direct health status determinations. More specifically, BSA is used within one or more algorithms to generate a health status indication of an animal according to a numerical or descriptive scale that defines the health status of an animal. One algorithm may include a BSA to weight ratio in which the measured BSA is divided by the weight, and this expression corresponds to a predetermined health status.

The BSA is automatically calculated by programming of software associated with a computer processor of the invention. One particular method of determining BSA may include determining the cross-sectional circumference of a measured animal by obtaining an estimated curve fitting for the measured circumferential "slice" wherein the curve fitting is calculated according to a geometric equation for a selected geometric shape, such as a circle or ellipse as set forth below.

According to one example in a preferred embodiment of the invention, BSA may be calculated from recorded sensor readings according to the following: Recorded sensor values provide data points in three dimensional space that can be defined in a standard three dimensional coordinate system (X, Y, and Z). The depth dimension Z can be eliminated in the recorded data points since measurements are to be taken in two dimensional space according to the planar or "slice" measurement protocol. This leaves the remaining dimensional variables X and Y. The variable X is distance measured by a sensor. The variable Y is the distance between adjacent sensors that are spaced from one another, for example, vertically along a mounting frame member. This vertical distance between sensors is a fixed distance based upon a pre-selected arrangement of the sensors within the mounting frame. A mathematical expression is applied to the plurality of measured X distances to fit the measured distances into a shape that approximates the circumferential shape of the animal. One shape that can be used to approximate the circumferential shape of an animal is a circle. The general equation for a circle, centered at (a,b) with a radius r, is the set of all points x and y such that $(x-a)^2+(y-b)^2=r$. Different sized circles can be obtained by varying the radius r. According to this equation, x is the measured distance X and y is the predetermined spacing Y between adjacent sensors. For a given circle with a known radius r and a known center point, calculations are made as to how far each measured distance X is from the model circle that approximates that cross sectional shape of the animal. Adding the distances to the selected model circle from each measured distance X provides the total error for the measured distances. Programming in software of the invention automatically generates a number of circle sizes so that the measured distances X for a particular measured "slice" best fits an optimum model circle that approximates the cross-sectional shape of the measured animal. The optimum model circle can be chosen by the one which has the smallest numerical total error. The volume or BSA of the measured animal can then estimated from a plurality of selected optimum model circles, each of which are obtained from the corresponding plurality of measured X distances as measurements are taken along a length of the animal passing through the measuring plane between sensors. For determining volume of an animal, one simplified calculation is simply the areas of the selected model geometric shape or "slice" (e.g. the aforementioned circle) multiplied by the distances between the selected geometric shapes. These distances are the incremental distances along the length of the animal, measured in the direction that the animal travels through the sensor measurement area. More specifically, for example, if there were 20 measured area "slices", there would be 19 distance measurements between the "slices". To estimate total BSA (again assuming a model geometric shape fitting was used), the total BSA would be the sum of the surface areas between each "slice". An estimate for surface area according to the invention could be, for example, the equation for the surface area of a cylinder since the torsos of many animals are generally cylindrical shaped. The surface area of a cylinder can be expressed by: $A=2(\pi)(r)(h)+2(\pi)(r)^2$ where r is the radius and h is the height. The height h is the distance between "slices" and the radius r could be the average radius between the two model circles that bound the distance measurement. In other words, the area of one cylinder of many cylinders that can be defined between a plurality of spaced model circles or "slices" is calculated by the length of the cylinder (the height h) and the numerical average of the radii of the two model circles or "slices" that bound the cylinder. The sum of all of the calculated surface areas of the cylinders is the calculated BSA. One particular advantage of the invention in determining BSA is the use of the PCR radar sensors that enable multiple measurements to be taken in short periods of time. The fast sampling capability of these PCR radar sensors therefore allows many "slice" calculations to be made which in turn, increases the accuracy of estimated volume or BSA.

Another shape that can be used to estimate the cross-sectional shape of an animal is an ellipse. For animals such as cattle, an ellipse may provide a better estimate for cross-sectional shape. The general equation for an ellipse include a center point coordinate and coordinate values for the major and minor axis vertices. The vertex points for one of the axis vertices may be set to correspond with the known and pre-determined vertical spacing Y between adjacent sensors but an additional variable is required to be fit for the two coordinate points on the other vertex axis. The same process as described with fitting an optimum model circle can be used with an ellipse shape to approximate the cross-sectional shape of the measured animal. Programming in the software of the invention automatically generates a number of ellipse sizes so that the measured distances X for a particular measured "slice" best fits an optimum model ellipse that approximates the cross-sectional shape of the measured animal. The body surface area of the measured animal is again then obtained from the plurality of selected optimum model ellipses, each of which are calculated with variables populated from the corresponding plurality of measured X distance as the animal passes through the measuring plane between the sensors.

It should be understood that the particular mathematical equation selected for a shape (e.g. a circle or ellipse) may be calculated as many times as necessary with variables selected from the measured X distances to obtain desired estimation accuracy for a cross-sectional shape of the animal. Accordingly, programming of the software may be configured so that iterative calculations are executed to obtain the desired accuracy for the selected shape based on the measured X distance data.

The process described above for obtaining a best curve fitting corresponding to the cross-sectional shape of a measured animal can be used even if one or more of the sensors are blocked by an object, such as a post. A sensor that is blocked will have measurement data read by a computer processor of the invention that can identify the particular sensor as having data with much higher error readings. The selected algorithm for determining cross-sectional shape can eliminate sensor data with out of range data values so that the curve fitting calculations can provide a more accurate fit matching the cross-sectional shape of the measured animal. As long as a majority of the sensors are not blocked, the algorithm can provide an accurate estimate of the animal surface area obtained from the fitted cross sectional shapes.

Considering the afore-mentioned features and attributes of the invention, in one aspect, the invention may be considered a system for determining a health status of an animal based on a measured body surface area (BSA) of the animal, comprising: a plurality of measurement sensors for measuring corresponding distances between opposite sides of an animal to be measured; a computer processor for receiving and storing measurement data taken by the measurement sensors, said computer processor including at least one algorithm for estimating the BSA of an animal considering a plurality of measurements taken by the measurement sensors; a first output associated with the BSA, said first output including a user interface that displays information including the differential measurements and a calculated BSA, wherein said measurement data includes a plurality of measurements taken along corresponding planes that are converted to the BSA of the animal; providing objective criteria defining various health states of a selected animal specie and recording such criteria in a database of said computer processor; automatically correlating, by said computer processor, a calculated BSA with a corresponding health status of an animal whose BSA has been calculated; and automatically generating, by said computer processor, a second output that describes the corresponding health status.

According to another aspect of the invention, it may be considered a method for determining a health status of an animal based on a measured body surface area (BSA) of the animal, comprising: providing a plurality of measurement sensors for measuring corresponding distances between opposite sides of an animal to be measured; providing a computer processor for receiving and storing measurement data taken by the measurement sensors, said computer processor including at least one algorithm for estimating the BSA of an animal considering a plurality of measurements taken by the measurement sensors; generating a first output associated with the BSA, said first output including a user interface that displays information including the differential measurements and a calculated BSA, wherein said measurement data includes a plurality of measurements taken along corresponding planes that are converted to the BSA of the animal; providing objective criteria defining various health states of a selected animal specie and recording such criteria in a database of said computer processor; automatically correlating, by said computer processor, a calculated BSA with a corresponding health status of an animal whose BSA has been calculated; and automatically generating, by said computer processor, a second output that describes the corresponding health status.

According to another aspect of the invention, it may be considered a system for determining the body surface area (BSA) of an animal, comprising: a measurement frame; a plurality of measurement sensors mounted to the measurement frame and arranged in opposing pairs for measuring corresponding distances between opposite sides of an animal to be measured; a computer processor for receiving and storing measurement data taken by the measurement sensors, said computer processor including at least one algorithm for estimating the BSA of an animal considering a plurality of measurements taken by the measurement sensors; an output associated with the BSA, said output including a user interface that displays information including the differential measurements and a calculated BSA; and wherein said measurement data includes a plurality of measurements taken along corresponding planes that are converted to the BSA of the animal.

According to another aspect of the invention, it may be considered a method of determining the body surface area (BSA) of an animal, comprising: providing a measurement frame; mounting a plurality of measurement sensors to the measurement frame and disposed in pairs of sensors for measuring corresponding distances between opposite sides of an animal to be measured; providing a computer processor for receiving and storing measurement data taken by the measurement sensors, said computer processor including at least one algorithm for estimating the BSA of an animal considering a plurality of measurements taken by the measurement sensors; taking and recording a plurality of measurements of the animal as the animal passes the supports, said measurements being taken along a selected plane; processing the measurements by the computer processor; generating an output indicating the BSA of the animal, said output including a user interface that displays information including differential measurements taken and a calculated BSA; and wherein said measurement data includes a plurality of measurements taken along corresponding planes that are converted to the BSA of the animal.

According to yet another aspect of the invention, it may be considered a system for determining a health status of an animal based on a measured body surface area (BSA) of the animal, comprising: a measurement frame; a plurality of measurement sensors mounted to the measurement frame and disposed in pairs of sensors for measuring corresponding distances between opposite sides of an animal to be measured; a computer processor for receiving and storing measurement data taken by the measurement sensors, said computer processor including at least one algorithm for estimating the BSA of an animal considering a plurality of measurements taken by the measurement sensors; an output associated with the estimated BSA, said output including a user interface that displays information including the differential measurements and a calculated BSA, and wherein said measurement data includes a plurality of measurements taken along corresponding planes that are converted to the calculated BSA of the animal; predetermined animal health criteria stored in said computer processor to correlate the calculated BSA to a health status of the animal; and wherein said computer processor automatically assigns a health status to the animal considering the predetermined animal health criteria and an associated calculated BSA.

According to yet another aspect of the invention, it may be considered a method for determining a health status of an animal based on a measured body surface area (BSA) of the animal, comprising: providing a measurement frame; mounting a plurality of sensors to the measurement frame and disposed in pairs of sensors for measuring corresponding distances between opposite sides of an animal to be measured; providing a computer processor for receiving and storing measurement data taken by the measurement sensors, said computer processor including at least one algorithm for estimating the BSA of an animal considering a plurality of measurements taken by the measurement sensors; generating an output associated with the estimated BSA, said output including a user interface that displays information including the differential measurements and a calculated BSA, wherein said measurement data includes a plurality of measurements taken along corresponding planes that are converted to the calculated BSA of the animal; providing predetermined animal health criteria stored in said computer processor to correlate the calculated BSA to a health status of the animal; and automatically assigning, by said computer processor, a health status to the animal considering the predetermined animal health criteria and an associated calculated BSA.

Additional optional features for any of the above described aspects of the invention may further include: wherein said measurement frame includes a pair of horizontally spaced posts and said plurality of measurement sensors are mounted to said posts and vertically spaced from one another; wherein said plurality of measurement sensors are mounted in opposing pairs to said posts, each sensor of a corresponding pair being configured to measure a distance to account for sideways or transverse movement of the animal as it passes through said measurement frame; wherein said plurality of measurement sensors includes at least one of a pulse coherent radar (PCR) sensor device or an infrared (IR) sensor device; wherein said corresponding planes are vertically oriented and a measured length of an animal is horizontally oriented; wherein said corresponding planes are oriented substantially perpendicular to a measured length of an animal; wherein said at least one algorithm includes mathematical calculations using said measurement data.

According to another aspect of the invention, it may be considered a non-transitory computer-readable medium containing computer executable instructions, wherein, when executed by a computer processor, the instructions cause the computer processor to execute a method for determining the body surface area (BSA) of an animal, the computer-readable instructions comprising: instructions to receive and store data corresponding to measurement data obtained from a plurality of measurement sensors that measure distances between opposite sides of an animal to obtain a plurality of circumferential measurements around the animal, the measurements being at locations on the animal that are longitudinally spaced along a length of the animal, and wherein said circumferential measurements are taken along corresponding planes where the sensors are located; instructions to execute at least one algorithm that provides an estimate of the BSA, wherein input variables to the algorithm at least include the plurality of circumferential measurements; and instructions to generate an output from the executed algorithm including a user interface that provides an estimate of a BSA of at least one animal that has been measured.

Additional optional features of this aspect of the invention, include; wherein said corresponding planes are oriented substantially perpendicular to a horizontal axis defined by a direction of travel of the animal being measured; wherein said corresponding planes are oriented substantially orthogonal to a direction of travel of the animal as the animal passes through a measurement area where the measurement sensors take measurements; and further including instructions to generate an output, including a user interface, that considers the estimated BSA to subsequently determine and display on said user interface a health status of the animal.

Various other features and advantages of the invention will become apparent from a review of the following detailed description taken in conjunction with the drawings.

DETAILED DESCRIPTION

Figure 1:
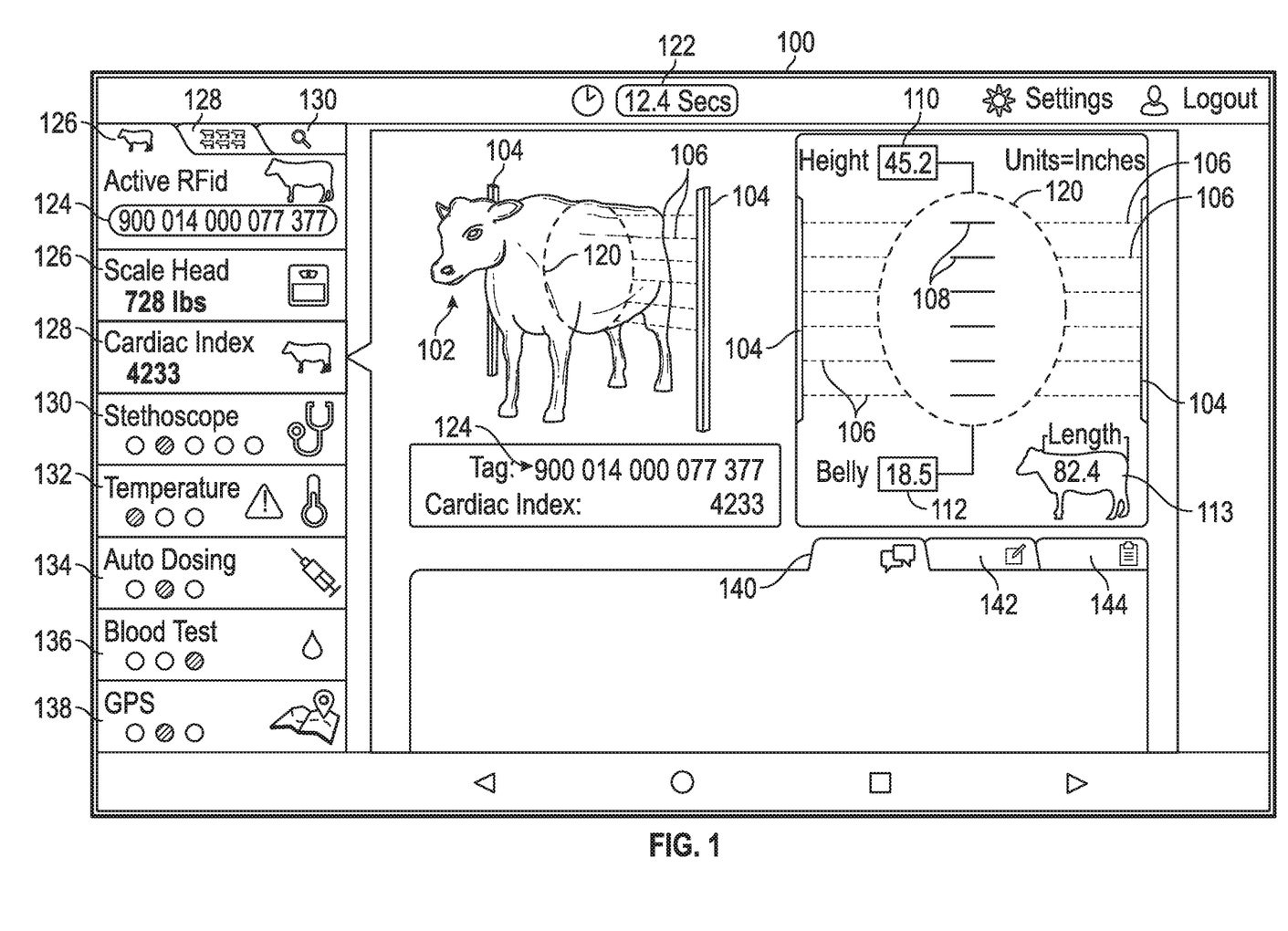
FIG. 1 is a user interface in a data processing system showing a conceptual view of a chute-side measuring system and one set of measurements taken along a vertical plane to determine a BSA of the animal. The user interface shows other data associated with a particular animal including other measured parameters of the animal and related historical animal records.

FIG. 1 is a sample user interface 100 associated with the processing of data as it relates to gathering, recording, and processing electronic measurements of a particular animal. More specifically, the central portion of FIG. 1 provides a visual representation of an animal 102 that is passing through a confined space such as a chute, in which a plurality of measuring devices (not shown) is mounted within a measurement frame. The particular measurement frame in FIG. 1 shows two spaced vertical posts 104. The vertical posts/supports may be positioned outside of an existing cattle chute or gate so that animals cannot physically contact the measuring devices or associated hardware mounted to or within the posts. Although vertical spaced posts are shown as an example measurement frame, it shall be understood that the measurement frame can be of any particular shape and orientation to achieve mounting of measuring sensors in positions to take desired measurements of passing animals.

The vertical posts 104 illustrated are exemplary in shape, size, and orientation to one another, and are shown for purposes of illustrating one example of how sensors can be disposed in pairs for differential measurements to be taken along a corresponding vertical plane between pairs of sensors. Dashed lines 106 represent the beams or waves that are emitted from the sensors.

The right side of FIG. 1 shows a schematic representation of the vertical posts 104 with measurement sensors (not shown) mounted within the posts that each emits the corresponding measurement sensor beam or wave 106. Numerical measurements are taken at a point in time when the sensors simultaneously operate to generate reflected beam or wave signals that are then processed by sensor circuitry. The processed signals correspond to numerical measurements for display to the user. These numerical measurements can be displayed (not shown) in the data fields 108.

Six pairs of measurement sensor beams/waves are illustrated at six distinct vertical heights along the lateral sides of the animal. Although only six pairs are shown, it should be understood that any desired number of sensor pairs can be used to most optimally provide data to define a measured vertical plane or "slice" of the animal. This portion of FIG. 1 also shows a height 110 and belly 112 measurement. The height measurement can be confirmed and defined by a measurement emission (e.g. IR laser or radar) that is not detected as a reflected signal back to a corresponding sensor. In other words, the lack of a reflected signal indicates there is no part of the animal that is present in the path of the emission and therefore indicates an upper height of the animal. As the animal moves through the confined space, the height measurement will vary based upon the particular shape of the upper surface of the animal. Similarly, the lower belly measurement can be obtained in the same way in which the lack of a reflected signal indicates there is no part of the animal that is present and therefore the lack of a reflected signal defines a lower edge or surface of the animal.

A plurality of slice or vertical plane measurements are taken as the animal progresses through the chute. A vertical plane measurement or vertical slice is depicted in FIG. 1 as the oval shaped circumference of the animal 120 shown in dashed lines. The recorded data points for each measurement are used within one or more numerical algorithms to determine a BSA for the animal. A ratio of BSA to weight can be used to define a presumptive health status of an animal. Incremental changes in calculated BSA to weight ratios over time may indicate progressive health deterioration or progressive health improvement.

A length 113 of the animal can also be determined by sensor measurement. The plurality of circumferential measurements can be interpreted to determine the length in which the smallest circumferential measurements in the first group of measurements will indicate the animal's head passing through the measurement plane while the final group of measurements will indicate the passage of the animal's hindquarters passing through the measurement plane.

The sensors are programmed to simultaneously operate to generate measurement signals according to one or more preconfigured conditions that confirm when the torso or other specific location on the animal is passing the vertical measurement plane (such as when the sensor readings indicate that the chest of the animal commences to pass the vertical measurement plane).

The upper margin of the user interface provides an elapsed time measurement 122 indicating how long it took to process the animal. In the example, processing was complete at 12.4 seconds after the animal entered the vertical plane between defined as the vertical plane located between the pairs of sensors. It is desirable to limit processing time for each animal so that many animals may be processed without delay.

Also illustrated below the schematic image of the animal 102 in FIG. 1 is the animal tag number 124. The tag number is one or more unique numbers or codes assigned to each different animal for tracking purposes throughout the life cycle of the animal.

Additional data corresponding to the animal is shown on the left side of the user interface. Beginning from top to bottom, a first display box 126 shows the animal's tag number 124 that matches the tag number shown below the image of the animal. The display box 126 also shows three tabs. The tab illustrated provides a selected tag number corresponding to the animal. A user may click on the second tab 128 to select another animal from a different grouping of animals, such as an animal at another feedlot location. The third tab 130 allows a user to conduct a search for a particular animal or group of animals from a search query entered by the user.

Displayed below the electronic tag information in box 126 is the weight of the animal. The example weight is labeled as a Scale Head measurement in pounds.

Below the weight indicator box is box 128 that shows a cardiac index score. The cardiac index score corresponds to the cardiopulmonary rate ratio (CPRR), such as disclosed in the U.S. patent application Ser. No. 15/307,141, the disclosure of this application being incorporated herein by reference for purposes of disclosing that CPRR can be displayed in the present invention. The CPRR is an alternate method of determining the presumptive health status of an animal.

Below the cardiac index score is a lung score in box 130 which relates to a presumptive diagnosis as to the condition of the animal's lungs. The condition is indicated by the illumination of one of five indicator lights or buttons 129. The condition is determined according to a scoring system and method disclosed in the U.S. patent application Ser. No. 13/442,569, the disclosure of which is also incorporated herein by reference for purposes of disclosing a lung health diagnosis system and method. This patent application also discloses use of an electronic stethoscope and associated computer processing technology in which auscultated sounds are recorded.

Below the lung score indication is a temperature indication in box 132 that includes a recorded measured temperature of the animal. It is known that an elevated temperature may indicate a compromised state of health, such as bovine respiratory disease (BRD) in cattle.

Below the temperature indication is an auto dosing indicator in box 134. The auto dosing indicator indicates whether an animal has received or may require inoculation during processing.

Below the auto dosing indicator is a blood test indicator in box 136 that displays information relating to whether a blood test has been taken and whether the blood test is normal or abnormal. For example, the blood test indicator as shown provides three indicator conditions and each could represent a status (e.g., blood test taken/not taken; blood test normal/abnormal and new blood test required/not required).

Below the blood test indicator is a GPS indicator box 138 that can provide information as to the specific location where the animal was measured, such as a specific GPS coordinates. Large feed yards may have multiple processing locations and it may be beneficial to know which one was used.

Each of the boxes 124-138 may include a symbol that provides a quick visual identification of the animal health parameter measured. As shown, these symbols include an image of an animal, a weight scale, a stethoscope, a thermometer, a syringe, a droplet of blood, and a map. Other symbols may be used to visually assist a user in identifying fields in the user interface.

The user display also may contain notes 140, a listing of medications 142, or other animal data 144 that be selected by opening one of the corresponding tabs.

It should be understood that each of the boxes 124-138 are optional. An advantage in displaying one or more of these measurements or diagnoses is to enable a caregiver to view a large amount of data that can be used to contrast and compare the BSA or volume calculations.

Figure 2:
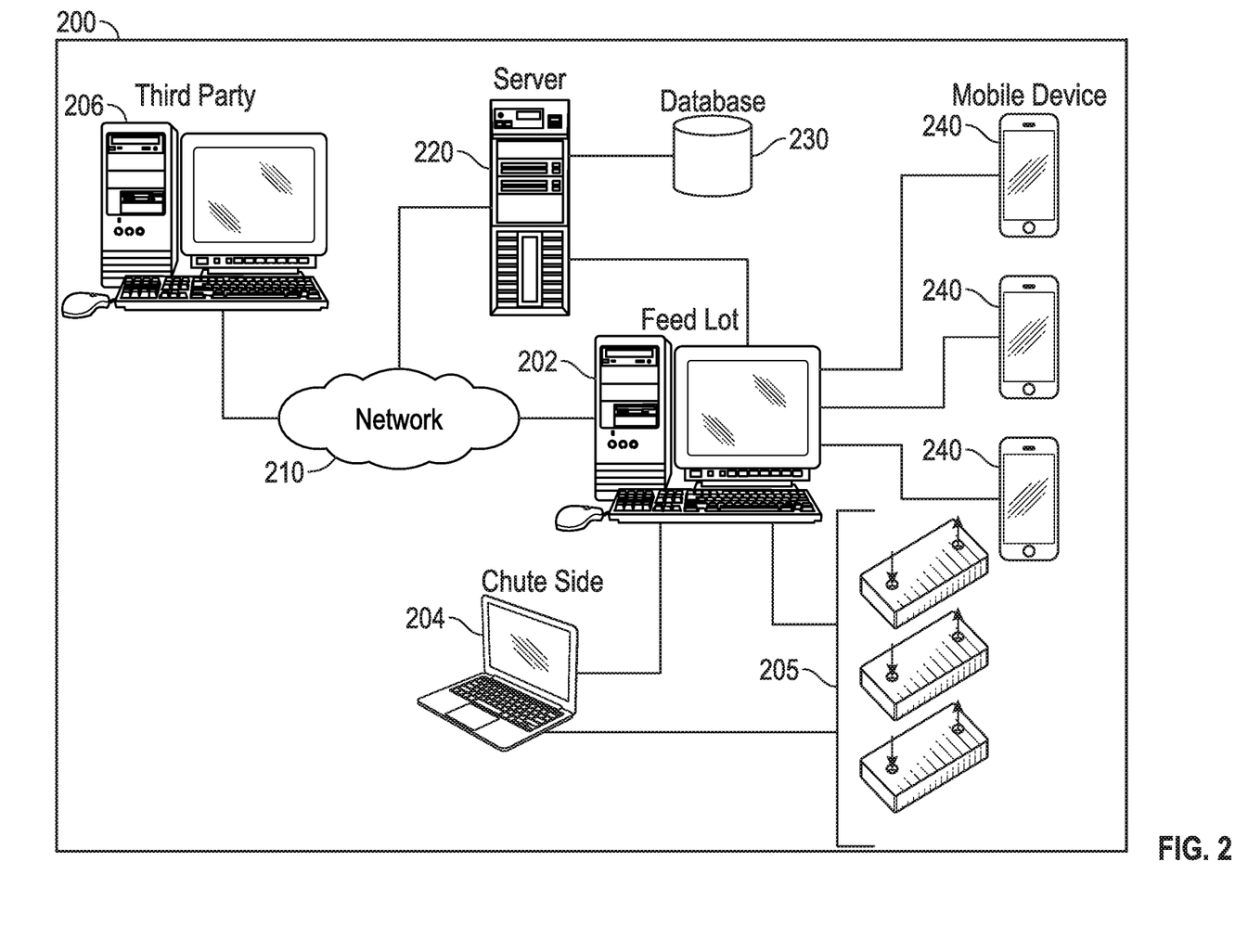
FIG. 2 is a schematic diagram of an example computer network in which the sensors and master controller may be installed to generate user outputs including user interfaces and other tangible outputs for use by a user.

FIG. 2 is an example computer network that may be used in connection with the system and method disclosed herein. More specifically, FIG. 2 illustrates a block diagram of a system 200 that includes one or more user computers shown as feed lot computer 202, a chute side computer 204, and third party computer 206. The feed lot computer represents one or more computers used in a feed lot environment used to automatically control the accounting, feeding, and treatment of animals prior to harvesting. The chute side computer 204 represents one or more computers used in a feed lot environment that may be used to initially receive and record data regarding animals being received into the feedlot. The third party computer 206 may represent one or more computers by third parties who may seek to exchange data with the feed lot, such as financial institutions, cattle growers, and other third parties who are involved with a livestock industry. These user computers 202, 204, and 206 may be general purpose personal computers (including, merely by way of example, personal computers and/or laptop computers running various versions of Microsoft Corp.'s Windows™ and/or Apple Corp.'s Macintosh™ operating systems) and/or workstation computers running any of a variety of commercially-available LINUX, UNIX™ or LINUX-like operating systems. These user computers 202, 204, and 206 may also have any of a variety of applications, including for example, database client and/or server applications, and web browser applications. Alternatively, the user computers 202, 204, and 206 may be any other electronic device, such as a thin-client computer, Internet-enabled mobile telephone, and/or personal digital assistant, capable of communicating via a network (e.g., the network 200 described below) and/or displaying and navigating web pages or other types of electronic documents. Although the exemplary system 200 is shown with three user computers, any number of user computers may be supported.

System 200 further includes a network 210. The network 210 may be any type of network familiar to those skilled in the art that can support data communications using any of a variety of commercially-available protocols, including without limitation TCP/IP, SNA, IPX, AppleTalk, and the like. Merely by way of example, the network 210 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth™ protocol known in the art, and/or any other wireless protocol); and/or any combination of these and/or other networks.

The system may also include one or more server computers 220. One type of server may include a web server used to process requests for web pages or other electronic documents from user computers 202, 204, and 206. The web server can be running an operating system including any of those discussed above, as well as any commercially-available server operating systems. The web server can also run a variety of server applications, including HTTP servers, FTP servers, CGI servers, database servers, Java servers, and the like. In some instances, the web server may publish operations available as one or more web services.

The system 200 may also include one or more file and/or application servers, which can, in addition to an operating system, include one or more applications accessible by a client running on one or more of the user computers 202, 204, and 206. The file/application server(s) may be one or more general purpose computers capable of executing programs or scripts in response to the user computers 202, 204, and 206. As one example, the server may execute one or more web applications. The web application may be implemented as one or more scripts or programs written in any programming language, such as Java™, C, C#™ or C++, and/or any scripting language, such as Perl, Python, or TCL, as well as combinations of any programming/scripting languages. The application server(s) may also include database servers, including without limitation those commercially available from Oracle, Microsoft, Sybase™, IBM™ and the like, which can process requests from database clients running on a user computer.

In one functional aspect, an application server may create web pages dynamically for displaying the functionality associated with the system to include the user interface of FIG. 1. The web pages created by the web application server may be forwarded to a user computer via a web server. Similarly, the web server may be able to receive web page requests, web services invocations, and/or input data from a user computer and can forward the web page requests and/or input data to the web application server.

In another functional aspect, the server 220 may also function as a file server.

The system 200 may also include a database 230. The database 230 may reside in a variety of locations. By way of example, database 230 may reside on a storage medium local to (and/or resident in) one or more of the computers 202, 204, and 206. Alternatively, it may be remote from any or all of the computers 202, 204, and 206, and in communication (e.g., via the network 210) with one or more of these. In a particular set of embodiments, the database 230 may reside in a storage-area network ("SAN"). Similarly, any necessary files for performing the functions attributed to the computers 202, 204, and 206 may be stored locally on the respective computer and/or remotely, as appropriate. The database 230 may be a relational database, such as Oracle 10i™, that is adapted to store, update, and retrieve data in response to SQL-formatted commands.

The system may further include one or more mobile devices 240 illustrated as "smart phones". These mobile devices 240 communicate with the computer 202, such as by a web interface, Bluetooth, or wireless connection. The mobile devices may communicate with any other of the computers in the system through the network 210, the figure simply illustrating an exemplary connection with computer 202. The mobile devices have their own internal computer processing capabilities with integral computer processors and other supporting hardware and software. The mobile devices may be specially configured to run a mobile software application(s) in order to view user interfaces and to view and update system data. All of the functionality associated with the system as applied to the computers 202, 204, and 206 may be incorporated in the mobile devices 240 as modified by mobile software applications especially adapted for the mobile device hardware and operating systems. In connection with operating systems, it should therefore be understood that the mobile devices are not limited to any particular operating system, Apple iOS and Android-based systems being two examples.

FIG. 2 also schematically illustrates a plurality of measuring sensors 205 each having sensor circuitry (not shown). The directional arrows for each sensor indicate each sensor has functionality for beam/wave emission and subsequent detection. (the directional arrows pointing away from the measuring sensors indicating emissions and the arrows pointing toward indicating detections). The circuitry for each device includes a sensor element, such as a PCR sensor or an IR sensor (not shown), a microcontroller (not shown), and an optional radio (not shown). The microcontroller controls operation of the device and communicates with a main controller (not shown) which receives and processes data signals for each of the measuring device. The radio may be used if a sensor of a particular device is not located near a corresponding microcontroller or near other sensors. One preferred embodiment includes the use of wired connections (not shown) between the measuring devices and between the sensor circuitry and emitters for each measuring device. Other sensors may also be used in the area where measurements are to be taken, for example, to detect when the animal arrives and when the hindquarters of the animal pass. An arrival sensor (not shown) can be programmed to turn on the other sensors for purposes of initiating the plurality of vertical plane measurements to be taken as the animal moves through the chute. The arrival sensor would be positioned in front of the other sensors, that is, placed in a position that precedes the location where the animals are measured by the other sensors.

In connection with the microcontrollers of the measurement device, it is contemplated that these may incorporate field-programmable gat arrays (FPGA) in order to process the measurement data in a manner that makes the data easier to transfer and to further process in other computer processors of the system. Use of FPGA integrated circuits also provides great flexibility in selectively processing operation of the measurement devices.

In accordance with any of the computers 202, 204, and 206, these may be generally described as general purpose computers with elements that cooperate to achieve multiple functions normally associated with general purpose computers. For example, the hardware elements may include one or more central processing units (CPUs) for processing data.

The computers 202, 204, and 206 may further include one or more input devices (e.g., a mouse, a keyboard, etc.); and one or more output devices (e.g., a display device, a printer, etc.). The computers may also include one or more storage device. By way of example, storage device(s) may be disk drives, optical storage devices, solid-state storage device such as a random access memory ("RAM") and/or a read-only memory ("ROM"), which can be programmable, flash-updateable and/or the like.

Each of the computers and server described herein may include a computer-readable storage media reader; a communications peripheral (e.g., a modem, a network card (wireless or wired), an infra-red communication device, etc.); working memory, which may include RAM and ROM devices as described above. The server may also include a processing acceleration unit, which can include a DSP, a special-purpose processor and/or the like.

The computer-readable storage media reader can further be connected to a computer-readable storage medium, together (and, optionally, in combination with storage device(s)) comprehensively representing remote, local, fixed, and/or removable storage devices plus storage media for temporarily and/or more permanently containing computer-readable information. The computers and serve permit data to be exchanged with the network 210 and/or any other computer, server, or mobile device.

The computers and server also comprise various software elements and an operating system and/or other programmable code such as program code implementing a web service connector or components of a web service connector. It should be appreciated that alternate embodiments of a computer may have numerous variations from that described above. For example, customized hardware might also be used and/or particular elements might be implemented in hardware, software (including portable software, such as applets), or both. Further, connection to other computing devices such as network input/output devices may be employed.

It should also be appreciated that the method described herein may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, ROMs, RAMs, EPROMs, EEPROMs, magnetic or optical cards, flash memory, or other types of machine-readable mediums suitable for storing electronic instructions. Alternatively, the methods may be performed by a combination of hardware and software.

The term "software" as used herein shall be broadly interpreted to include all information processed by a computer processor, a microcontroller, or processed by related computer executed programs communicating with the software. Software therefore includes computer programs, libraries, and related non-executable data, such as online documentation or digital media. Executable code makes up definable parts of the software and is embodied in machine language instructions readable by a corresponding data processor such as a central processing unit of the computer. The software may be written in any known programming language in which a selected programming language is translated to machine language by a compile, interpreter or assembler element of the associated computer.

Considering the foregoing exemplary computer network and elements described therein, In connection with one embodiment of the of the invention, it may be considered a software program or software platform with computer coded instructions that enable execution of the functionality associated with the user interface of FIG. 1.

In connection with another embodiment of the invention, it may be considered a combined software and hardware system including a software program or software platform with computer coded instructions that enable execution of the functionality associated with the user interface of FIG. 1, and hardware elements including the plurality of sensors that are used to generate electronic signals corresponding to distance measurements. As set forth herein, the distance measurements include those measurements taken of the distances between the sensors and the targeted locations on the animal which are located along the vertical measurement plane.

In connection with yet another embodiment of the invention, it may be considered a sub-combination including one or more user interfaces generated by the software and the measurement sensors that provide inputs to a data processor of a computer that runs the software.

In connection with yet another embodiment of the invention, it may be considered a selected combination or sub-combination further including structure used to support the measurement sensors as mounted during operation. This structure includes a mounting frame or support referenced in FIG. 1, such as the vertical posts 104.

There are a number of advantages of the invention over existing C-scan and other measuring techniques. One existing C-scan technique only measures one viewable surface of the animal, such as the top of the animal where a shadow is cast. Contrast this to the invention which an entire circumference of the animal may be measured at a number of locations along the length of the animal. With the sensors operating in pairs, differential measurements can be taken to account for lateral movement of the animal within the chute area. Similarly, if an animal is not standing tall in its normal position while measurements are taken in prior art systems, the lack of sensors operating in pairs for vertical measurements result in less accurate data taken.

Another advantage is set up and calibration of the system. In the aforementioned C-scan technique, ambient lighting had to be strictly controlled to prevent background shadows from being cast. In the present invention, PCR sensors are not restricted to use in any lighting condition so accurate measurements can be taken even if relatively high sunlight conditions exist.

Yet another advantage of the invention is that a discrete number of measurements are recorded as distinct data points as opposed to many prior art systems which require video processing. Video processing is much slower than processing distinct data points. Accordingly, calculations used with the recorded data points for determining the BSA or volume of the animal can be generated very quickly and can be processed by smaller and lower powered computer processors.

Yet another advantage of the invention is that no special lighting is required. Special lighting that is required with respect to the aforementioned C-scan technique adds to the cost and complexity of the measurement system, and can be unreliable in changing light conditions. Yet another advantage of the invention is that a high number of data point measurements can be taken simultaneously for each vertical plane measurement. Therefore, actual geometric shape of the vertical cross section may be calculated more accurately.

Yet another advantage of the invention is that the sensors, whether they are PCR radar sensors or IR laser sensors, is that the sensors of the invention may be disposed in a protective arrangement within the chute structure and therefore are better protected. The chute can be constructed of sufficient strength and size so that contact made by the animals or workers attending to the animals at chute-side will not cause misalignment between measuring pairs of sensors.

While the invention has been set forth herein with respect to one or more preferred embodiments, the invention is not strictly limited to these embodiments and other changes and modifications can be made commensurate with the scope of the claims appended hereto.

What is claimed is:

1. A system for determining the body surface area (BSA) of an animal, comprising:
    a measurement frame including a first post and a second post spaced from said first post;
    a first plurality of measurement sensors mounted to said first post and a second plurality of measurement sensors mounted to said second post;
    said first plurality of measurement sensors being vertically spaced from one another on said first post and said second plurality of measurement sensors being vertically spaced from one another on said second post;
    wherein said first and second plurality of measurement sensors are disposed in corresponding pairs for measuring corresponding distances between opposite sides of an animal to be measured;
    wherein said sensors each emits a wave or beam that is oriented substantially perpendicular to a path of travel of the animal that is being measured and wherein said measurement sensors measure a time of flight and magnitude of reflection from the detected animal for a distance that is being measured and wherein said measurement sensors generate circumferential measurements of said animal;
    a computer processor for receiving and storing said measurements taken by said measurement sensors, said computer processor including at least one algorithm for estimating the BSA of an animal considering a plurality of said circumferential measurements taken by the measurement sensors;
    an output associated with the BSA, said output including a user interface that displays information including the measurement data and a calculated BSA; and
    wherein said circumferential measurements are taken along corresponding planes that are converted to the BSA of the animal.

2. The system, as claimed in claim 1, wherein:
    each sensor of a corresponding pair is configured to measure a distance to account for sideways or transverse movement of the animal as it passes through said measurement frame.

3. The system, as claimed in claim 1, wherein:
said plurality of measurement sensors includes at least one of a pulse coherent radar (PCR) sensor device or an infrared (IR) sensor device.

4. The system, as claimed in claim 1, wherein:
said corresponding planes are vertically oriented and a measured length of an animal is horizontally oriented.

5. The system, as claimed in claim 1, wherein:
said corresponding planes are oriented substantially perpendicular to a measured length of an animal.

6. The system, as claimed in claim 1, wherein:
said at least one algorithm includes mathematical calculations using said measurement data.

7. A method of determining the body surface area (BSA) of an animal, comprising:
providing a measurement frame;
mounting a plurality of measurement sensors in said measurement frame and disposed in pairs of sensors for measuring corresponding distances between opposite sides of an animal to be measured, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
providing a computer processor for receiving and storing measurement data taken by the measurement sensors, said computer processor including at least one algorithm for estimating the BSA of an animal considering a plurality of measurements taken by the measurement sensors;
taking and recording a plurality of measurements of the animal as the animal passes the measurement frame, said measurements being taken along a selected plane;
processing the measurements by the computer processor;
generating an output indicating the BSA of the animal, said output including a user interface that displays information including measurements taken and a calculated BSA; and
wherein said measurement data includes a plurality of circumferential measurements of said animal and said circumferential measurements taken along corresponding planes that are converted to the BSA of the animal.

8. The method, as claimed in claim 7, wherein:
said measurement frame includes a pair of horizontally spaced posts and said plurality of measurement sensors are mounted to said posts and vertically spaced from one another.

9. The method, as claimed in claim 7, wherein:
said plurality of measurement sensors are mounted in opposing pairs to said measurement frame, each sensor of a corresponding pair being configured to measure a distance to account for sideways or transverse movement of the animal as it passes through said measurement frame.

10. The method, as claimed in claim 7, wherein:
said plurality of measurement sensors includes at least one of a pulse coherent radar (PCR) sensor device or an infrared (IR) sensor device.

11. The method, as claimed in claim 7, wherein:
said corresponding planes are vertically oriented and a measured length of an animal is horizontally oriented.

12. The method, as claimed in claim 7, wherein:
said corresponding planes are oriented substantially perpendicular to a measured length of an animal.

13. The method, as claimed in claim 7, wherein:
said at least one algorithm includes mathematical calculations using said measurement data.

14. A system for determining a health status of an animal based on a measured body surface area (BSA) of the animal, comprising:
a measurement frame;
a plurality of measurement sensors mounted to said measurement frame and disposed in pairs of sensors for measuring corresponding distances between opposite sides of an animal to be measured, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
a computer processor for receiving and storing measurement data taken by the measurement sensors, said computer processor including at least one algorithm for estimating the BSA of an animal considering a plurality of measurements taken by the measurement sensors;
an output associated with the estimated BSA, said output including a user interface that displays information including the measurements taken and a calculated BSA, wherein said measurement data includes a plurality of circumferential measurements of said animal and said circumferential measurements taken along corresponding planes that are converted to the calculated BSA of the animal;
predetermined animal health criteria stored in said computer processor to correlate the calculated BSA to a health status of the animal; and
wherein said computer processor automatically assigns a health status to the animal considering the predetermined animal health criteria and an associated calculated BSA.

15. A method for determining a health status of an animal based on a measured body surface area (BSA) of the animal, comprising:
providing a measurement frame;
mounting a plurality of sensors to said measurement frame and disposed in pairs of sensors for measuring corresponding distances between opposite sides of an animal to be measured, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
providing a computer processor for receiving and storing measurement data taken by the measurement sensors, said computer processor including at least one algorithm for estimating the BSA of an animal considering a plurality of measurements taken by the measurement sensors;
generating an output associated with the estimated BSA, said output including a user interface that displays information including the measurements and a calculated BSA, wherein said measurement data includes a plurality of circumferential measurements of said animal and said circumferential measurements taken along corresponding planes that are converted to the calculated BSA of the animal;
providing predetermined animal health criteria stored in said computer processor to correlate the calculated BSA to a health status of the animal; and automatically assigning, by said computer processor, a health status to the animal considering the predetermined animal health criteria and an associated calculated BSA.

16. A system for determining a health status of an animal based on a measured body surface area (BSA) of the animal, comprising:
   a plurality of measurement sensors for measuring corresponding distances between opposite sides of an animal to be measured, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
   a computer processor for receiving and storing measurement data taken by the measurement sensors, said computer processor including at least one algorithm for estimating the BSA of an animal considering a plurality of measurements taken by the measurement sensors;
   a first output associated with the BSA, said first output including a user interface that displays information including the measurements and a calculated BSA, wherein said measurement data includes a plurality of circumferential measurements of said animal and said circumferential measurements taken along corresponding planes that are converted to the BSA of the animal;
   wherein a database of said computer processor includes recorded data including objective criteria defining various health states of a selected animal species; and
   a second output generated by said computer processor that describes a health status of an animal including a calculated BSA.

17. A method for determining a health status of an animal based on a measured body surface area (BSA) of the animal, comprising:
   providing a plurality of measurement sensors for measuring corresponding distances between opposite sides of an animal to be measured, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
   providing a computer processor for receiving and storing measurement data taken by the measurement sensors, said computer processor including at least one algorithm for estimating the BSA of an animal considering a plurality of measurements taken by the measurement sensors;
   generating a first output associated with the BSA, said first output including a user interface that displays information including the measurements and a calculated BSA, wherein said measurement data includes a plurality of circumferential measurements of said animal and said circumferential measurements taken along corresponding planes that are converted to the BSA of the animal;
   providing objective criteria defining various health states of a selected animal species and recording such criteria in a database of said computer processor;
   automatically correlating, by said computer processor, a calculated BSA with a corresponding health status of an animal whose BSA has been calculated; and
   automatically generating, by said computer processor, a second output that describes the corresponding health status.

18. A non-transitory computer-readable medium containing computer executable instructions, wherein, when executed by a computer processor, the instructions cause the computer processor to execute a method for determining the body surface area (BSA) of an animal, the computer-readable instructions comprising:
   instructions to receive and store data corresponding to measurement data obtained from a plurality of measurement sensors that measure distances between opposite sides of an animal to obtain a plurality of circumferential measurements around the animal, the measurements being at locations on the animal that are longitudinally spaced along a length of the animal, and wherein said circumferential measurements are taken along corresponding planes where the sensors are located, wherein said sensors each emits a wave or beam that is oriented substantially perpendicular to a path of travel of the animal that is being measured and wherein said plurality of measurement sensors measure a time of flight and magnitude of reflection from the detected animal for a distance that is being measured;
   instructions to execute at least one algorithm that provides an estimate of the BSA, wherein input variables to the algorithm at least include the plurality of circumferential measurements; and
   instructions to generate an output from the executed algorithm including a user interface that provides an estimate of a BSA of at least one animal that has been measured.

19. The non-transitory computer-readable medium, as claimed in claim 18 wherein:
   said corresponding planes are oriented substantially perpendicular to a horizontal axis defined by a direction of travel of the animal being measured.

20. The non-transitory computer-readable medium, as claimed in claim 18 wherein:
   wherein said corresponding planes are oriented substantially orthogonal to a direction of travel of the animal as the animal passes through a measurement area where the measurement sensors take measurements.

21. The non-transitory computer-readable medium, as claimed in claim 18, further including: instructions to generate an output, including a user interface, that considers the estimated BSA to subsequently determine and display on said user interface, a health status of the animal.

* * * * *